(12) United States Patent
Kusunose

(10) Patent No.: US 7,907,270 B2
(45) Date of Patent: Mar. 15, 2011

(54) INSPECTION APPARATUS AND METHOD, AND PRODUCTION METHOD FOR PATTERN SUBSTRATES

(75) Inventor: Haruhiko Kusunose, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 98 days.

(21) Appl. No.: 12/015,059

(22) Filed: Jan. 16, 2008

(65) Prior Publication Data

US 2008/0186476 A1 Aug. 7, 2008

(30) Foreign Application Priority Data

Feb. 2, 2007 (JP) ................................. 2007-024108

(51) Int. Cl.
*G01N 21/00* (2006.01)
(52) U.S. Cl. ................. 356/237.4; 356/237.1; 356/237.5
(58) Field of Classification Search ..... 356/237.1–237.5
See application file for complete search history.

(56) References Cited

U.S. PATENT DOCUMENTS

| | | | | |
|---|---|---|---|---|
| 5,426,503 | A | * | 6/1995 | Kusunose ..................... 356/520 |
| 6,175,645 | B1 | * | 1/2001 | Elyasaf et al. ................ 382/147 |
| 7,046,355 | B2 | * | 5/2006 | Yu ............................... 356/237.2 |
| 7,075,638 | B2 | * | 7/2006 | Kvamme et al. ........... 356/237.2 |
| 2003/0189703 | A1 | * | 10/2003 | Yonezawa et al. ......... 356/237.2 |
| 2005/0134840 | A1 | * | 6/2005 | Yu ............................... 356/237.2 |
| 2005/0174570 | A1 | * | 8/2005 | Kvamme et al. ........... 356/237.5 |
| 2006/0209298 | A1 | * | 9/2006 | Kvamme et al. ........... 356/237.2 |

FOREIGN PATENT DOCUMENTS

| | | | |
|---|---|---|---|
| JP | 9-311108 A | | 12/1997 |
| JP | 2004-301751 A | | 10/2004 |
| JP | 2004-354088 A | | 12/2004 |
| JP | 2006-014133 A | | 1/2006 |
| JP | 2006-72147 A | | 3/2006 |
| JP | 2006072147 A | * | 3/2006 |
| JP | 2006-112912 A | | 4/2006 |
| JP | 2007-298526 A | | 11/2007 |

* cited by examiner

*Primary Examiner* — Tarifur R. Chowdhury
*Assistant Examiner* — Isiaka O Akanbi
(74) *Attorney, Agent, or Firm* — Sughrue Mion, PLLC

(57) ABSTRACT

According to a first aspect of the present invention, there is provided an inspection apparatus including an objective lens, a reflected illumination optical system that illuminates a first area which is part of a field of view of the objective lens, a transmitted illumination optical system that illuminates the first area and a second area; an adjusting unit that adjusts positions on the sample of transmitted illumination light from the transmitted illumination optical system and reflected illumination light from the reflected illumination optical system; a first detector that detects a transmitted light transmitted by the sample and a reflected light reflected by the sample in the first area; and a second detector that detects through the objective lens a transmitted light transmitted by the sample in the second area.

15 Claims, 3 Drawing Sheets

INSPECTION APPARATUS AND METHOD, AND PRODUCTION METHOD FOR PATTERN SUBSTRATES

BACKGROUND OF THE INVENTION

1. Field of the Invention

The present invention relates to an inspection apparatus and method, and a production method for pattern substrates and particularly to an inspection apparatus and method using transmitted light transmitted by a sample and reflected light reflected by the sample, and a production method for pattern substrates that uses the method.

2. Description of Related Art

In a semiconductor manufacturing process, if a pattern has a defect, a wire insulation failure or a short circuit may occur, thus reducing yields. Accordingly, an inspection apparatus is used to inspect whether a foreign object is sticking to a pattern substrate such as a semiconductor substrate and a photomask used in the semiconductor manufacturing process.

For such photomask inspection apparatuses, there are mainly two modes: a die-to-database mode and a die-to-die mode. In the die-to-database mode, an actually detected image and CAD data stored in a processor such as a computer are compared to detect a foreign object or a defect. However, in the die-to-database mode, for each pattern to be inspected, a reference image needs to be created from CAD data, and hence it is difficult to lower costs.

Meanwhile, in the die-to-die mode, images of occurrences of the same pattern located at different positions are detected, and by comparing them, the detection of a foreign object or a defect is performed. In this mode, a reference image for each pattern need not be created from CAD data, and hence costs can be lowered. However, with this mode, as to a mask having only one occurrence of the same pattern on its substrate, a foreign object or a defect therein cannot be detected.

In order to solve this problem, a method is disclosed where a transmission image and a reflection image are picked up by a camera to be overlaid is disclosed (refer to, for example, Japanese Unexamined Patent Application Publication No. Hei 9-311108). In this inspection apparatus, transmitted light and reflected light are combined to detect with a single detector. The intensity of light transmitted by a transmitting pattern of a mask and the intensity of light reflected by a light shielding pattern of the mask are adjusted. By this means, in a combined optical image (combined image), brightness is the same for pattern areas, where a light shielding is formed, and non-pattern (transmitting pattern) areas, where no light shielding is formed. In the transmitting pattern, transmitted light through a place to which a foreign object is sticking decreases in amount because transmittance decreases due to the foreign object. Meanwhile, in the light shielding pattern, reflected light from a place to which a foreign object is sticking decreases in amount because reflectance decreases due to the foreign object. Therefore, the detected amount of light from a place with a foreign object thereon decreases as compared with a normal place not depending on whether the place with the foreign object thereon is in the light shielding pattern or in the transmitting pattern.

Hence, by comparing the output of the detector and a foreign object detection threshold, foreign object inspection can be performed. With this configuration, a combined image of a transmission image and a reflection image is detected with a single detector, and hence the inspection apparatus can be simply configured.

Moreover, an inspection apparatus which picks up a transmission image and a reflection image separately for inspection is disclosed (refer to Japanese Unexamined Patent Application Publications No. 2004-354088 and No. 2006-72147). In this inspection apparatus, a transmitted illumination optical system and a reflected illumination optical system are each provided with a stop. A half of the field of view of an objective lens is illuminated with illumination light from the transmitted illumination optical system, and the other half is illuminated with illumination light from the reflected illumination optical system. Then, a transmission image formed by light transmitted by the photomask is picked up by a transmission image sensor, and a reflection image formed by light reflected by the photomask is picked up by a reflection image sensor. That is, the transmission image and the reflection image are received by separate sensors. Then, the output of each sensor and a threshold are compared for inspection. As such, both a transmission image and a reflection image are picked up, and hence the photomask can be accurately inspected.

This inspection apparatus will be described using FIG. 3. FIG. 3 diagrammatically shows the field of view of an objective lens on a photomask. The field of view 70 of the objective lens is circular, and a half thereof is a transmission illuminated area 71 illuminated by the transmitted illumination light from the transmitted illumination optical system, and the other half is a reflection illuminated area 72 illuminated by the reflected illumination light from the reflected illumination optical system. That is, the field of view 70 of the objective lens is divided into halves according to a straight line 77 passing through its center. One of the halves is the transmission illuminated area 71 and the other is the reflection illuminated area 72. Let a transmission image picking-up area 75 be an area picked up by a transmission image sensor and a reflection image picking-up area 76 be an area picked up by a reflection image sensor. The transmission image picking-up area 75 is included in the transmission illuminated area 71, and the reflection image picking-up area 76 is included in the reflection illuminated area 72.

In the above inspection apparatus, a detection optical system can be common, thus simplifying the configuration of the apparatus. Further, both transmission images and reflection images can be obtained by scanning the entire photomask once. That is, a transmission image and a reflection image can be picked up at the same time, hence shortening inspection time.

In order to further shorten inspection time of the above inspection apparatus, the transmission image picking-up area 75 and the reflection image picking-up area 76 are preferably enlarged in the field of view 70 of FIG. 3. By enlarging an area whose image can be picked up at one time, the scan distance becomes shorter, thus shortening inspection time. The transmission image picking-up area 75 and the reflection image picking-up area 76 are preferably enlarged as much as possible. Accordingly, the transmission image picking-up area 75 and the reflection image picking-up area 76 become closer to the straight line 77.

However, there is the following problem with such a defect inspection apparatus. If the transmission image picking-up area 75 and the reflection image picking-up area 76 are enlarged to shorten inspection time, the transmission image picking-up area 75 and the reflection image picking-up area 76 become closer to each other. That is, the transmission image picking-up area 75 and the reflection image picking-up area 76 are located adjacent to the straight line 77. In this state, if an illumination area deviates, illumination light from the transmitted illumination optical system may be incident partly on the reflection image picking-up area 76, or illumination light from the reflected illumination optical system may be incident partly on the transmission image picking-up area 75. For example, if the transmission illuminated area 71, on which transmitted illumination light is incident, spreads over the straight line 77, the transmitted illumination light is incident partly on the reflection image picking-up area 76. Thus, the reflection image picking-up area 76 is not uniformly illuminated, and hence the photomask cannot be accurately inspected.

Especially, there is variation in thickness of photomasks. To be specific, a variation of about ±100 µm exists with 6.35 mm thick photomasks. Thus, where the objective lens is placed on the pattern-formed-surface side of a photomask, if thickness varies between photomasks, the focal point of the transmitted illumination optical system deviates from the pattern formed surface. Furthermore, aberration occurs due to the difference in thickness of photomasks, and hence focusing becomes difficult.

For example, when an image of the view field stop of the transmitted illumination optical system is formed on the pattern formed surface, the image is blurred with variation in thickness of photomasks. Thus, the transmission image picking-up area 75 spreads. Hence, the transmitted illumination light is incident partly on the reflection image picking-up area 76, so that the reflection image picking-up area 76 is not uniformly illuminated. Therefore, there is the problem with conventional inspection apparatuses that accurate inspection cannot be performed in a short time.

The present invention was made in view of the above problem, and an object thereof is to provide an inspection apparatus and method which can perform accurate inspection in a short time, and a production method for pattern substrates.

SUMMARY OF THE INVENTION

According to a first aspect of the present invention, there is provided an inspection apparatus which performs inspection using transmitted light transmitted by a sample and reflected light reflected by the sample, comprising: an objective lens; a reflected illumination optical system that illuminates a first area which is part of a field of view of the objective lens from the objective lens side of the sample; a transmitted illumination optical system that illuminates the first area and a second area which is the other part of the field of view of the objective lens than the first area from the opposite side of the sample from the objective lens; an adjusting unit that adjusts positions on the sample of transmitted illumination light from the transmitted illumination optical system and reflected illumination light from the reflected illumination optical system; a first detector that detects through the objective lens a transmitted light transmitted by the sample in the first area of the transmitted illumination light from the transmitted illumination optical system and a reflected light reflected by the sample in the first area of the reflected illumination light from the reflected illumination optical system; and a second detector that detects through the objective lens a transmitted light transmitted by the sample in the second area of the transmitted illumination light from the transmitted illumination optical system.

According to a second aspect of the present invention, the transmitted illumination light from the transmitted illumination optical system is incident on the entire field of view of the objective lens.

According to a third aspect of the present invention, the reflected illumination light from the reflected illumination optical system is incident on substantially a half of the field of view of the objective lens.

According to a fourth aspect of the present invention, the apparatus picks up by the first detector a combined image of a transmission image formed by the transmitted illumination light and a reflection image formed by the reflected illumination light and picks up by the second detector a transmission image formed by the transmitted illumination light, and which subtracts the transmission image from the combined image of the same position on the sample to obtain the reflection image of the sample.

According to a fifth aspect of the present invention, there is provided an inspection method which performs inspection by detecting through an objective lens transmitted light transmitted by a sample and reflected light reflected by the sample, comprising the steps of: illuminating the sample with reflected illumination light from the objective lens side of the sample to illuminate a first area which is part of a field of view of the objective lens; illuminating the sample with transmitted illumination light from the opposite side of the sample from the objective lens to illuminate the first area and a second area which is the other part of the field of view of the objective lens than the first area; making reflected light reflected by the sample which is part of the reflected illumination light and transmitted light transmitted by the sample which is part of the transmitted illumination light incident on the objective lens, while changing positions on the sample of the transmitted illumination light and the reflected illumination light; detecting through the objective lens the transmitted light and the reflected light from the first area, which is part of the field of view of the objective lens; and detecting through the objective lens the transmitted light from the second area, which is the other part of the field of view of the objective lens than the first area.

According to a sixth aspect of the present invention, the transmitted illumination light is incident on the entire field of view of the objective lens.

According to a seventh aspect of the present invention, the reflected illumination light is incident on substantially a half of the field of view of the objective lens.

According to an eighth aspect of the present invention, by detecting through the objective lens the transmitted light and the reflected light from the first area, a combined image of a transmission image formed by the transmitted illumination light and a reflection image formed by the reflected illumination light is picked up, and by detecting through the objective lens the transmitted light from the second area, a transmission image formed by the transmitted illumination light is picked up, and wherein by subtracting the transmission image from the combined image of the same position on the sample, the reflection image of the sample is obtained.

According to a ninth aspect of the present invention, there is provided a production method for a pattern substrate, comprising the steps of: inspecting a photomask according to the inspection method of Claim 5; repairing a defect of the photomask inspected in the inspecting step; exposing a substrate with the photomask repaired in the repairing step; and developing the exposed substrate.

The above and other objects, features and advantages of the present invention will become more fully understood from the detailed description given hereinbelow and the accompanying drawings which are given by way of illustration only, and thus are not to be considered as limiting the present invention.

DETAILED DESCRIPTION OF THE PREFERRED EMBODIMENTS

Figure 1:
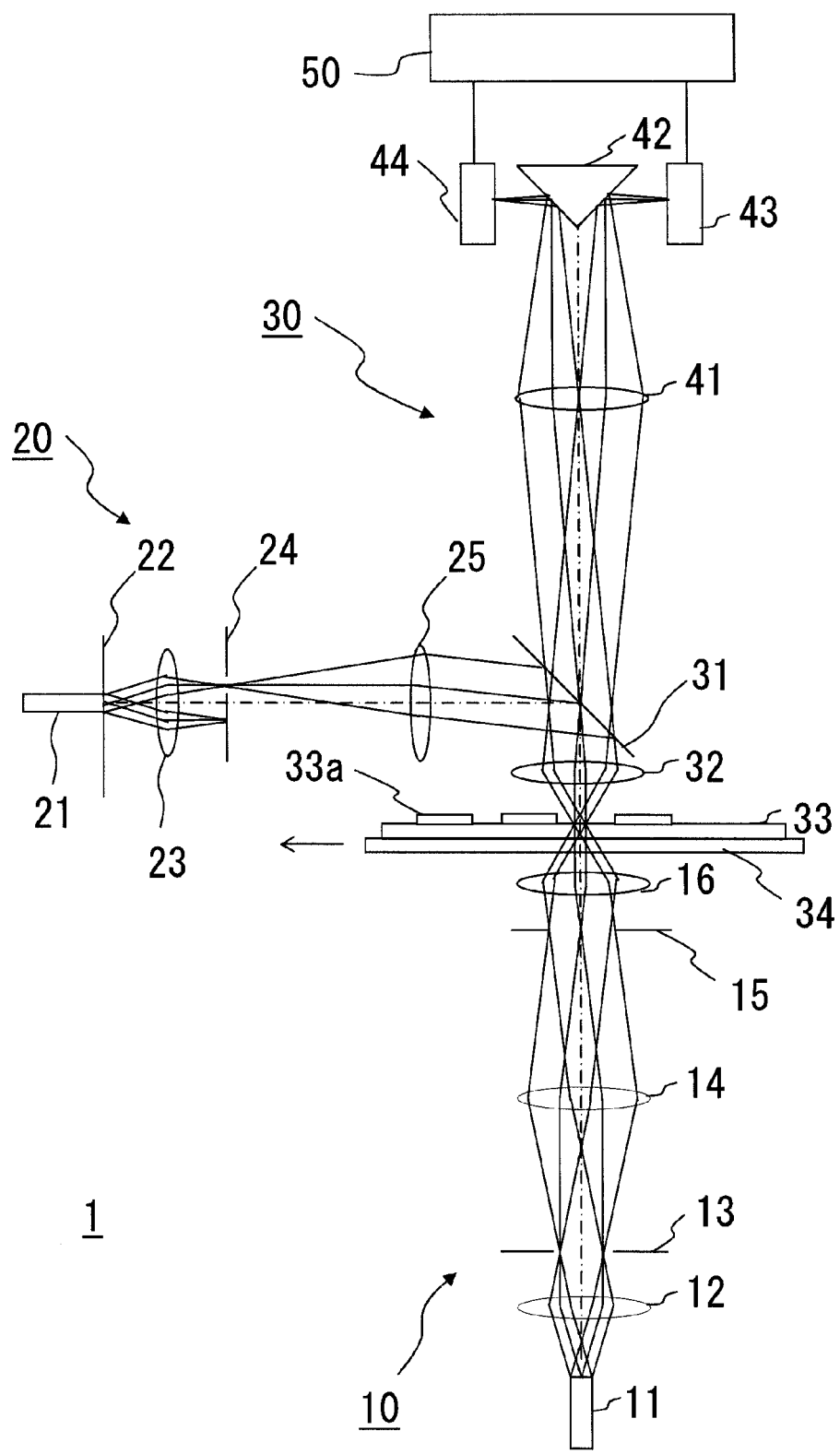
FIG. 1 shows diagrammatically the configuration of an inspection apparatus according to the present invention.

An embodiment of the present invention will be described below. The description below will be made to present an embodiment of the present invention, and the invention is not intended to be limited in scope to the embodiment below. For clarification of description, omission and simplification will be made in the description below as needed, and those skilled in the art could easily change, add to, or alter the components of the embodiment below within the scope of the present invention. The same reference numerals indicate the same or like elements in the figures, with description thereof being omitted as needed.

An inspection apparatus according to the present invention inspects a sample using reflected light reflected by the sample and transmitted light transmitted by the sample. To be specific, the transmitted light transmitted by the sample is detected by a sensor to pick up a transmission image formed by the transmitted light. Further, the transmitted light transmitted by the sample and the reflected light reflected by the sample are superimposed one on the other and detected by a sensor. A combined image of a transmission image formed by the transmitted light and a reflection image formed by the reflected light is picked up. Then, inspection is performed based on the transmission image and the combined image.

The inspection apparatus according to the present invention will be described using FIG. 1. Description will be made taking as an example an inspection apparatus 1 for detecting a foreign object sticking to a photomask 33 as a sample. The photomask 33 is mounted on an X-Y stage 34 having an aperture therein. In FIG. 1, reference numeral 11 denotes a transmitted illumination light source, 12 a lens, 13 a view field stop, 14 a lens, 15 an aperture stop, and 16 a lens. The lens 12, the view field stop 13, the lens 14, the aperture stop 15, and the lens 16 form a transmitted illumination optical system 10. The transmitted illumination light source 11 outputs transmitted illumination light for transmission illuminating the photomask 33. That is, the transmitted illumination light from the transmitted illumination light source 11 passes through the transmitted illumination optical system 10 and is incident on the photomask 33. Then, light transmitted by the photomask 33 is detected by a sensor. A light shielding pattern 33a is formed on the photomask 33. Hence, the transmitted illumination light passes through non-pattern (transmitting pattern) areas of the photomask 33 where the light shielding pattern 33a is not formed. The surface of the photomask 33 where the light shielding pattern 33a is formed is called a pattern formed surface. The transmitted illumination optical system 10 illuminates the photomask 33 from the back surface side thereof. That is, light from the transmitted illumination light source 11 is incident on the photomask 33 from the opposite side of the photomask 33 from the pattern formed surface.

Reference numeral 21 denotes a reflected illumination light source, 22 an aperture stop, 23 a lens, 24 a view field stop, 25 a lens, 31 a beam splitter, and 32 a lens. The aperture stop 22, the lens 23, the view field stop 24, and the lens 25 form a reflected illumination optical system 20. The reflected illumination light source 21 outputs reflected illumination light for reflection illuminating the photomask 33. That is, the reflected illumination light from the reflected illumination light source 21 passes through the reflected illumination optical system 20 and is incident on the photomask 33. Then, light reflected by the photomask 33 is detected by a sensor. The lens 32 is an objective lens having a predetermined field of view on the pattern formed surface. The lens 32 is placed on the pattern-formed-surface side of the photomask 33, on which surface the light shielding pattern 33a is formed. That is, the reflected illumination light from the reflected illumination optical system 20 is incident on the photomask 33 from the pattern-formed-surface side of the photomask 33.

Reference numeral 41 denotes a lens, 42 a reflecting member, 43 a transmission image sensor, and 44 a combined image sensor. The lens 32, the beam splitter 31, the lens 41, and the reflecting member 42 form a detection optical system 30. The detection optical system 30 leads the light transmitted by the photomask 33 and the light reflected by the photomask 33 to the transmission image sensor 43 and the combined image sensor 44. As such, the light transmitted by the photomask 33 and the light reflected by the photomask 33 are incident on the transmission image sensor 43 or the combined image sensor 44 through the lens 32, the beam splitter 31, the lens 41, and the reflecting member 42. In the description below, the light output from the transmitted illumination light source 11 is referred to as transmitted illumination light, and the light output from the reflected illumination light source 21 is referred to as reflected illumination light. In addition, a part transmitted by the photomask 33 of the transmitted illumination light output from the transmitted illumination light source 11 is referred to as transmitted light, and a part reflected by the photomask 33 of the reflected illumination light output from the reflected illumination light source 21 is referred to as reflected light.

First, the transmitted illumination optical system 10 for making the transmitted illumination light output from the transmitted illumination light source 11 incident on the photomask 33 will be described. For example, one multi-mode optical fiber as a small light source can be used as the transmitted illumination light source 11. One end of the optical fiber is placed on the optical axis, and a light source is placed adjacent to the other end. By this means, light incident on the input end of the optical fiber from the light source travels through the optical fiber and is output through the output end. Light output at an angle smaller than the output angle determined by the NA (numerical aperture) of the optical fiber is irradiated onto the photomask 33. Instead of one optical fiber, a fiber bundle that is a bundle of fibers may be used as the transmitted illumination light source 11. The transmitted illumination light output from the transmitted illumination light source 11 is refracted by the lens 12 and is incident on the view field stop 13. The view field stop 13 has an aperture with the optical axis as its center. The transmitted illumination light incident on the outside of the aperture cannot pass through the view field stop 13 and is blocked. Only the light that has passed through the aperture of the view field stop 13 is incident on the lens 14.

The transmitted illumination light that has passed through the view field stop 13 is refracted by the lens 14 and incident on the aperture stop 15. The aperture stop 15 has an aperture of a predetermined size with the optical axis as its center. The transmitted illumination light that has passed through the aperture stop 15 is incident on the lens 16. The lens 16 is an imaging lens and condenses the transmitted illumination light such that an image of the view field stop 13 is formed on the pattern formed surface of the photomask 33. That is, the focal point of the transmitted illumination optical system 10 is on the pattern formed surface of the photomask. The photomask 33 is illuminated by the transmitted illumination light from the transmitted illumination light source 11 with use of the transmitted illumination optical system 10. The transmitted illumination optical system 10 illuminates the entire field of view of the lens 32, the objective lens. The transmitted illumination optical system 10 illuminates from the opposite side of the photomask 33 from the objective lens. That is, the transmitted illumination light is incident on the photomask 33 at the surface of the photomask 33 opposite to the pattern formed surface.

Next, the reflected illumination optical system 20 for making the reflected illumination light output from the reflected illumination light source 21 incident on the photomask 33 will be described. An optical fiber can be used for the reflected illumination light source 21 like for the transmitted illumination light source 11. The reflected illumination light from the reflected illumination light source 21 may be the same in wavelength as the transmitted illumination light from the transmitted illumination light source 11. By this means, the optical design of the detection optical system 30 can be simplified. The reflected illumination light output from the reflected illumination light source 21 is incident on the aperture stop 22 having an aperture therein. The aperture of the aperture stop 22 is of a size corresponding to the output end of the optical fiber. The center of the aperture of the aperture stop 22 is located on the optical axis. The light that has passed through the aperture stop 22 is incident on the lens 23. The reflected illumination light incident on the lens 23 is refracted and incident on the view field stop 24. The view field stop 24 has an aperture displaced with respect to the optical axis. The reflected illumination light incident on the outside of the aperture cannot pass through the view field stop 24 and is blocked. Only the light that has passed through the aperture of the view field stop 24 is incident on the lens 25. In FIG. 1, the aperture of the view field stop 24 is provided at a position displaced upward from the optical axis.

The reflected illumination light that has passed through the view field stop 24 is refracted by the lens 25 and incident on the beam splitter 31. The beam splitter 31 is, for example, a half mirror. The beam splitter 31 reflects part of the light incident thereon toward the photomask 33. The reflected illumination light reflected by the beam splitter 31 is incident on the lens 32. The lens 32 is an objective lens and condenses the light such that an image of the view field stop 24 is formed on the pattern formed surface of the photomask 33. That is, an image of the view field stop 24 is formed on the pattern formed surface by the lens 32. In this way, the reflected illumination light from the reflected illumination light source 21 illuminates the photomask 33. Here, the reflected illumination light is condensed to a spot displaced from the optical axis because the view field stop 24 is displaced with respect to the optical axis. Therefore, the reflected illumination optical system 20 illuminates only part of the field of view of the lens 32. As such, the reflected illumination light is incident on only part of the field of view of the lens 32 on the pattern formed surface of the photomask 33. Here, the reflected illumination light is condensed to a spot displaced rightward with respect to the optical axis. The lens 32 is placed on the pattern-formed-surface side of the photomask 33.

The reflected illumination optical system 20 illuminates the photomask 33 from the lens 32 side. That is, the reflected illumination light is incident on the pattern formed surface of the photomask 33 through the lens 32. The reflected illumination optical system 20 may be provided with an autofocus mechanism. By this means, the focal point of the reflected illumination optical system 20 coincides with the pattern formed surface of the photomask 33, and hence accurate inspection can be performed.

The photomask 33 is illuminated by the transmitted illumination light and the reflected illumination light. Here, the transmitted illumination light is incident on the entire field of view of the lens 32, while the reflected illumination light is incident on only part of the field of view of the lens 32. Therefore, part of the field of view of the lens 32 is illuminated by only the transmitted illumination light, while the other part of the field of view is illuminated by both the reflected illumination light and the transmitted illumination light. Herein, the area illuminated by only the transmitted illumination light is referred to as a transmission illuminated area, and the area illuminated by both the reflected illumination light and the transmitted illumination light is referred to as a coincidentally illuminated area. That is, the area illuminated coincidentally by the reflected illumination light and the transmitted illumination light to obtain a combined image is a coincidentally illuminated area. Here, a half of the field of view of the lens 32 is the transmission illuminated area, and the other half is the coincidentally illuminated area. A transmission image is picked up from the transmitted light from the transmission illuminated area, and a combined image of a transmission image and a reflection image is picked up from the transmitted illumination light and the reflected illumination light from the coincidentally illuminated area. The combined image is an optical image obtained by combining a transmission image formed by the transmitted light and a reflection image formed by the reflected light.

The photomask 33 is mounted on the X-Y stage 34 connected to a drive mechanism and can be scanned in the direction of the arrow in FIG. 1. By driving the X-Y stage 34, the photomask 33 moves in the direction of the arrow. The X-Y stage 34 has an opening corresponding to the part of the photomask to be inspected. Alternatively, the X-Y stage 34 may be made of a transparent material such as glass. By scanning the X-Y stage 34 in the direction of the arrow, the position where the transmitted illumination light is incident and the position where the reflected illumination light is incident move on the pattern formed surface of the photomask 33 so that the position of the field of view of the lens 32 changes relative to the photomask 33. Thereby, the illuminated position of the photomask 33 can be controlled, and by raster scanning the photomask 33, the entire photomask 33 can be illuminated and thus inspected. Of course, the scan direction may be opposite to the direction of the arrow. Note that scan means other than the X-Y stage 34 can be used.

As such, lights from the transmitted illumination light source 11 and the reflected illumination light source 21 illuminate the photomask 33. The lights illuminating the photomask 33 are transmitted or reflected depending on the pattern formed on the photomask 33. For example, the light output from the transmitted illumination light source 11 passes through the transmitting pattern, other areas than the light shielding pattern 33a, of the photomask 33 and is incident on the lens 32. Meanwhile, the light output from the transmitted illumination light source 11 is incident on the light shielding pattern 33a and is reflected. Part of light output from the reflected illumination light source 21 is incident on the light shielding pattern 33a and is reflected toward the lens 32. Meanwhile, other part of the light output from the reflected illumination light source 21 is incident on the transmitting pattern, other areas than the light shielding pattern 33a, and passes through the photomask 33. Light incident on a defective place to which a foreign object or the like is sticking is, for example, scattered according to the property thereof, and hence defect inspection can be performed.

As such, the light transmitted by the photomask 33 from the transmitted illumination light source 11 and the light reflected by the photomask 33 from the reflected illumination light source 21 are incident on the lens 32. The transmitted light and the reflected light are refracted by the lens 32 and incident on the beam splitter 31. The beam splitter 31 transmits part of the incident light, so that parts of the transmitted light and the reflected light pass through the beam splitter 31 and are incident on the lens 41. The lens 41 forms an image of the pattern formed surface of the photomask 33 onto the light receiving face of the transmission image sensor 43 and the light receiving face of the combined image sensor 44. The transmission image sensor 43 picks up a transmission image and the combined image sensor 44 picks up a combined image. The transmitted light and the reflected light are refracted by the lens 41 and are incident on the reflecting member 42. The reflecting member 42 is an optical element such as a reflecting mirror or prism and reflects the incident light in a predetermined direction. The reflecting member 42 is provided with two reflecting faces at different angles. That is, the reflecting member 42 has two reflecting faces at different angles. The lights incident on the different reflecting faces are reflected in different directions respectively.

The reflecting member 42 makes the light from the coincidentally illuminated area and the light from the transmission illuminated area diverge. For example, in FIG. 1, the reflecting member 42 reflects the transmitted light from the transmission illuminated area rightward and the transmitted light and the reflected light from the coincidentally illuminated area leftward. Thus, the transmitted light from the transmission illuminated area is reflected in the direction of the transmission image sensor 43, and the transmitted light and the reflected light from the coincidentally illuminated area are reflected in the direction of the combined image sensor 44. As such, the reflecting member 42 makes the transmitted light diverge in one or the other direction depending on the position in the field of view of the lens 32 on the pattern formed surface. That is, the transmitted lights from the field of view of the lens 32 are made to diverge in two different directions depending on the incident position on the pattern formed surface. The transmission image sensor 43 detects the transmitted light from the transmission illuminated area to pick up a transmission image, and the combined image sensor 44 detects the transmitted light and the reflected light from the coincidentally illuminated area to pick up a combined image.

The transmission image sensor 43 and the combined image sensor 44 are, for example, a photo-detector such as a CCD camera and have pixels arranged in an array. The transmission image sensor 43 and the combined image sensor 44 output a signal based on the amount of received light of each pixel to a processor 50. The processor 50 is an information processing device having a personal computer or the like, and the detected signal from each sensor is input to the processor 50. An A/D converter of the processor 50 converts the detected signal to digital form and stores the A/D-converted detected signal into storage such as memory.

The memory stores received light amount data based on the amount of received light of each pixel, and further may store received light amount data for an area of the photomask 33. A computing unit of the processor 50 performs computation to detect a defect using the stored received light amount data for the transmission image and the combined image. For example, received light amount data for the combined image is compared with a threshold. If the received light amount data exceeds the threshold, the processor 50 determines that a defect or a foreign object exists. Or, features are extracted from the combined image to inspect for a foreign object. Further, received light amount data for the transmission image is used in defect inspection by image comparison. That is, images from patterns in the same shape are compared for defect inspection of the patterns. Output signals of the X-Y stage 34 driving the photomask 33 are input to the processor 50. The position (coordinates) of a detected place on the photomask 33 is identified based on the output signals of the X-Y stage 34, and thereby the location of a defect or a foreign object on the photomask 33 is identified. As such, different processes are performed on the detected signals of the transmission image and the combined image to inspect, thereby performing accurate inspection. Needless to say, other methods than the above may be used to inspect. The algorithm for defect detection is not limited to a particular one. The processor 50 is provided with a display such as an LCD or a CRT so as to display the transmission image and the combined image separately or simultaneously.

By subtracting the transmission image from the combined image, a reflection image can be obtained. That is, data of the combined image and the transmission image is stored in memory, and the transmission image is subtracted from the combined image picked up from the same position on the sample. By this means, a reflection image of the position of the photomask 33 can be obtained. For example, a combined image is obtained from the transmitted light and the reflected light received by the combined image sensor 44. Then, the X-Y stage 34 is moved by half of the field of view of the lens 32 to obtain a transmission image from the transmitted light received by the transmission image sensor 43. This transmission image and the combined image are images of the same position of the photomask 33. That is, the transmission image and the combined image of the same position on the sample are obtained. Then, by subtracting data of the transmission image from data of the combined image, data of the reflection image is obtained. Thus, the transmission image, the reflection image, and the combined image can be used. A defect detecting algorithm can be performed on the reflection image. As such, by obtaining the reflection image from the difference of the combined image and the transmission image, an algorithm can be performed for each of the transmission image and the reflection image. Therefore, inspection accuracy can be improved.

The processor 50 is not limited to a physically single device. For example, the A/D converter, the memory, and the computing unit may be each incorporated in a different device. Further, parallel processing may be performed using a computing unit having a plurality of CPUs. The transmission image sensor 43 and the combined image sensor 44 may be a one-dimensional line sensor or a two-dimensional area sensor, and an image pickup device such as a CCD sensor, a CMOS sensor, or a photodiode array can be used. Or, an image pickup device of a time-delay integration (TDI) type may be used. In this case, the scan direction of the stage and the vertical transfer direction of signal electric charges are made to be the same, and the scan speed and the transfer speed are made synchronous. By this means, detection sensitivity can be improved. Moreover, the above inspection apparatus can be used for the inspection of substrates having a transparent pattern and a light shielding pattern, not being limited to the inspection of photomasks. Color filter substrates and the like as well as photomasks can be subjects to be inspected by this inspection apparatus.

Other light source may be used as the transmitted illumination light source 11 and the reflected illumination light source 21, not being limited to an optical fiber. For example, a laser light source, a lamp light source, and a fiber bundle can be used. Light from the same light source may be divided into two parts as the transmitted illumination light source 11 and the reflected illumination light source 21. In this case, one light source can be shared as the transmitted illumination light source 11 and the reflected illumination light source 21, thus reducing the number of components. However, where illumination conditions for transmitted illumination and reflected illumination are separately adjusted, two light sources are preferably used.

Figure 2:
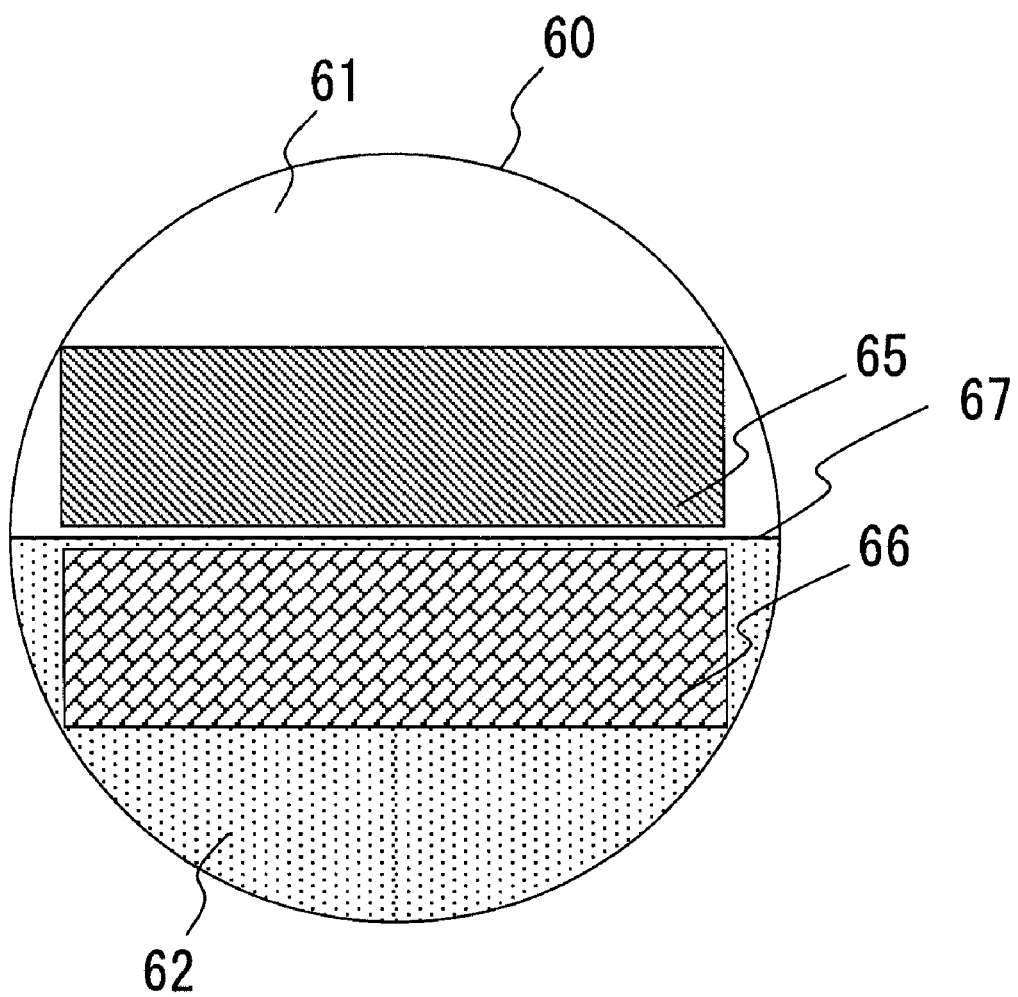
FIG. 2 shows diagrammatically the field of view of an objective lens of the inspection apparatus according to the present invention.
Figure 3:
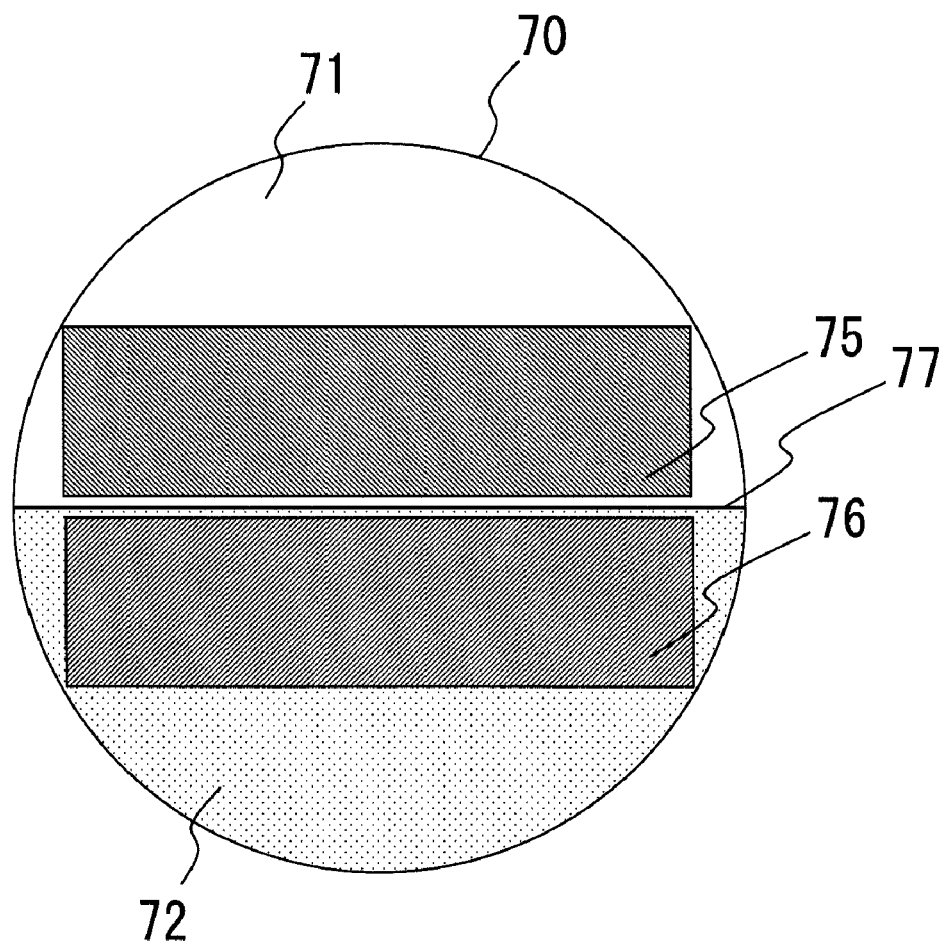
FIG. 3 shows diagrammatically the field of view of an objective lens of a conventional inspection apparatus.

Next, the illumination state on the pattern formed surface of a photomask will be described using FIG. 2. FIG. 2 shows diagrammatically the field of view of the lens 32 on the pattern formed surface of the photomask 33.

The field of view 60 of the lens 32 on the pattern formed surface of the photomask 33 is circular. As described previously, the reflected illumination light is incident on only part of the field of view 60 of the lens 32. In FIG. 2, the reflected illumination light is incident on only the lower half of the field of view 60. That is, the reflected illumination light is not incident on the upper half of the field of view 60. Thus, the reflected illumination light is incident only on the lower side of a straight line 67 passing through the center of the circular field of view 60. Meanwhile, the transmitted illumination light uniformly illuminates the entire field of view of the lens 32. The area of the field of view 60 of the lens 32 on which the reflected illumination light is incident is included in the area on which the transmitted illumination light is incident. That is, the reflected illumination light illuminates only part of the area on which the transmitted illumination light is incident. The reflected illumination light from the reflected illumination light source 21 passes through the view field stop 24 and is incident on part of the area on which the transmitted illumination light is incident in the pattern formed surface. As such, in the pattern formed surface, the area on which the reflected illumination light is incident overlaps partly the area on which the transmitted illumination light is incident.

Only the transmitted illumination light is incident on the upper half of the field of view 60. A transmission illuminated area 61 on which only the transmitted illumination light is incident is the semicircular upper half of the field of view 60. A coincidentally illuminated area 62 on which the transmitted illumination light and the reflected illumination light are incident is the semicircular lower half of the field of view 60. The straight line 67 passing through the center of the circular field of view 60 is the boundary between the transmission illuminated area 61 and the coincidentally illuminated area 62. The semicircle on the upper side of the straight line 67, the boundary, is the transmission illuminated area 61, and the semicircle on the lower side is the coincidentally illuminated area 62. The transmitted light is incident on the transmission illuminated area 61 and the coincidentally illuminated area 62. The reflected illumination optical system 20 illuminates the lower half of the field of view 60 of the lens 32, the coincidentally illuminated area 62. Also the transmitted illumination optical system 10 illuminates the lower half of the field of view 60 of the lens 32, the coincidentally illuminated area 62. In addition, the transmitted illumination optical system 10 illuminates the transmission illuminated area 61 displaced from the coincidentally illuminated area 62 in the field of view 60. That is, the transmitted illumination light from the transmitted illumination optical system 10 illuminates the coincidentally illuminated area 62, the lower half, and the transmission illuminated area 61, the upper half. Thus, the other part than the transmission illuminated area 61 in the field of view 60 is the coincidentally illuminated area 62. The transmitted light from the transmission illuminated area 61 is reflected by the reflecting member 42 toward the transmission image sensor 43. Meanwhile, the transmitted light and the reflected light from the coincidentally illuminated area 62 are reflected by the reflecting member 42 toward the combined image sensor 44.

Let a transmission image picking-up area 65 be the area picked up by the transmission image sensor 43 and a combined image picking-up area 66 be the area picked up by the combined image sensor 44. The transmission image picking-up area 65 and the combined image picking-up area 66 are rectangles of substantially the same size. Needless to say, the transmission image picking-up area 65 is included in the transmission illuminated area 61, and the combined image picking-up area 66 is included in the coincidentally illuminated area 62. That is, part of the coincidentally illuminated area 62 is the combined image picking-up area 66 and part of the transmission illuminated area 61 is the transmission image picking-up area 65. In FIG. 2, the combined image picking-up area 66 is located on the lower side of the straight line 67, and the transmission image picking-up area 65 is located on the upper side of the straight line 67. The straight line 67 is in between the transmission image picking-up area 65 and the combined image picking-up area 66. An image of the photomask 33 in the transmission image picking-up area 65 is formed by the lens 41 onto the light receiving face of the transmission image sensor 43. An image of the photomask 33 in the combined image picking-up area 66 is formed by the lens 41 onto the light receiving face of the combined image sensor 44. The transmission image picking-up area 65 and the combined image picking-up area 66 are positioned along the straight line 67. By driving the X-Y stage 34, the photomask 33 moves in the direction of the arrow in FIG. 1. That is, the photomask 33 is scanned in a direction perpendicular to the straight line 67. For example, when driving the X-Y stage 34, the area being illuminated moves, and thereby part of the photomask 33 in the transmission illuminated area 61 instantly moves into the coincidentally illuminated area 62. Therefore, a transmission image and a combined image of the same position of the photomask 33 are picked up at substantially the same time. That is, by scanning perpendicularly to the straight line 67, the time that a transmission image is picked up can be made close to the time that a combined image of the same position is picked up. In other words, the interval between the times that a transmission image and a combined image of the same position of the photomask 33 are picked up can be made short. To be specific, the distance between the transmission image picking-up area 65 and the combined image picking-up area 66 corresponds to the interval between the times that a transmission image and a combined image of the same position are picked up. Thus, accurate inspection can be performed.

In this embodiment, the transmitted illumination light is incident on the entire field of view 60. Thus, even if the photomasks 33 vary in thickness, accurate inspection can be performed. That is, even if the thickness of the photomask 33 has varied and an image of the view field stop 13 on the pattern formed surface is blurred, there is no change in the state where the entire field of view 60 is uniformly transmission illuminated. Even if an aberration occurs due to a difference in thickness between the photomasks 33, the transmitted illumination light uniformly illuminates the entire field of view. Thus, even if the thickness of the photomasks 33 varies, there is no influence on the transmission image and the combined image through the transmitted illumination light.

Where an autofocus mechanism is used in the reflected illumination optical system 20, the height of the lens 32 follows the height of the pattern surface of the photomasks 33.

That is, the autofocus mechanism makes the distance between the photomasks 33 and the lens 32 constant. Hence, the area on which the reflected illumination light is incident does not change within the field of view of the lens and does not spread into the transmission image picking-up area 65. Thus, even if the thickness of the photomasks varies, there is hardly any influence on the transmission image and the combined image. As such, since uniformly illuminated, the transmission image and the combined image can be accurately picked up. Further, because the distance between the transmission image picking-up area 65 and the combined image picking-up area 66 can be made smaller, the transmission image picking-up area 65 and the combined image picking-up area 66 can be made larger. Hence, the size of the areas that can be picked up at one time becomes larger, thus shortening the scan distance. The inspection apparatus 1 according to the present embodiment can perform accurate inspection in a short time. The transmission illuminated area 61 is substantially a half of the field of view 60, and the coincidentally illuminated area 62 is the other half of the field of view 60. Thus, the transmission image picking-up area 65 and the combined image picking-up area 66 can be made to be of the same size, hence shortening the time required to pick up a transmission image and a combined image.

In the present embodiment, the transmitted light and the reflected light travel through the same detection optical system 30. That is, the transmitted light and the reflected light from the combined image picking-up area 66 and the transmitted light from the transmission image picking-up area 65 travel through the same detection optical system 30. As such, the detection optical system is common to the transmission image and the reflection image. Therefore, the combined image and the transmission image can be picked up with a simple optical system substantially simultaneously. Thus, the picking-up time is shortened and inspection efficiency is improved.

The reflecting member 42 may be structured to reflect only one of light from the transmission illuminated area 61 and light from the coincidentally illuminated area 62. By this means, the transmitted light from the transmission illuminated area 61 can be separated from the transmitted light and the reflected light from the coincidentally illuminated area 62. For example, only the transmitted light and the reflected light from the coincidentally illuminated area 62 may be incident on and reflected by the reflecting member 42. Or, only the transmitted light from the transmission illuminated area 61 may be incident on and reflected by the reflecting member 42. Light from the coincidentally illuminated area 62 and light from the transmission illuminated area 61 need only be made to travel in different directions, so that the transmission image sensor 43 and the combined image sensor 44 can be placed so as not to interfere. That is, the transmission image sensor 43 and the combined image sensor 44 can be placed apart.

Moreover, since the transmitted lights are made to diverge by the reflecting member 42, the transmission illumination light source 11 and the reflected illumination light source 21 can be light sources of the same wavelength. Thus, optical characteristics can be made to be the same with a simple optical system. Furthermore, for the transmitted illumination optical system and the reflected illumination optical system, different light sources are used and separate aperture stops are provided. Hence, illumination conditions can be adjusted separately for them. Needless to say, light from one light source may be divided into the transmitted illumination light and the reflected illumination light, thereby reducing the number of components. In this case, by inserting filters into the transmitted illumination optical system 10 and the reflected illumination optical system 20, the amount of light can be adjusted.

The inspection method using the inspection apparatus according to the present invention illuminates the photomasks 33 with the reflected illumination light from the lens 32 side of the photomasks 33 to illuminate the coincidentally illuminated area 62, part of the field of view of the lens 32, and also illuminates the photomasks 33 with the transmitted illumination light to illuminate the coincidentally illuminated area 62 and the transmission illuminated area 61. Light reflected by the photomasks 33 and light transmitted by the photomasks 33 pass through the lens 32 and travel toward the sensors. The transmitted light from the transmission illuminated area 61, part of the field of view of the lens 32, is detected through the objective lens by the transmission image sensor 43. The transmitted light and the reflected light from the coincidentally illuminated area 62, part of the field of view of the lens 32, is detected through the lens 32 by the combined image sensor 44. As such, because the transmitted light and the reflected light travel through the same optical system, optical characteristics can be made to be the same with the simple optical system. Because the transmitted illumination light source 11 and the reflected illumination light source 21 can be light sources of the same wavelength, more accurate foreign object inspection can be performed. That is, the detection optical system 30 (optical components such as the lens 41, the lens 32, and the beam splitter 31) can be designed for a single wavelength. Hence, the deviation between a transmission image and a reflection image due to a distortion of the optical system can be made small.

With use of the above inspection apparatus, photomasks are inspected to detect a defect of the photomask. Then, by repairing the defect of the photomask, the photomask which is free of a defect is produced. Hence, productivity in producing photomasks can be improved. A substrate having photosensitive resin applied thereon is exposed through such a photomask which is free of a defect and developed with a developing agent. Thereby, the photosensitive resin can be accurately patterned. Hence, pattern substrates having their photosensitive resin patterned can be produced with good productivity. Further, where the photosensitive resin is a resist, a conductive film or an insulating film is etched with the patterned photosensitive resin as a mask, and hence productivity in producing pattern substrates such as wiring substrates can be improved.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An inspection apparatus for inspecting a photomask having a pattern formed surface on which light intercepting patterns are formed and a rear surface opposite to the pattern formed surface, so as to detect defects existing on the photomask, the apparatus comprising;

an illumination system providing a transmission illumination beam and a reflection illumination beam simultaneously, and directing respectively said transmission and reflection illumination beams onto the photomask from the opposite sides of the photomask, wherein said transmission illumination beam is directed onto the rear surface of the photomask to illuminate a first larger area of the photomask, and the reflection illumination beam is directed onto a pattern formed surface of the photomask to illuminate a second smaller area which overlaps with a part of the first area, so that composite light consisting of transmitted light through the photomask and reflected light by the photomask emanates from the second area, and the transmitted light through the photomask emanates from a third area which is the remaining area of the first area except the second area simultaneously;

a detection system comprising a first image sensor for receiving and detecting the composite light emanating from the second area so as to capture a composite image consisting of a transmitted image and a reflected image of the second area of the photomask, and a second image sensor for receiving and detecting the transmitted light emanating from the third area so as to capture the transmitted image of the third area of the photomask;

a light directing system directing the composite light emanating from the second area and the transmitted light emanating from the third area onto the detection system; and a processor coupled to the detection system and processing image signals outputted from the detection system to produce data indicative of the defects; wherein said inspection apparatus captures the composite image consisting of the transmitted image and the reflected image of the second area of the photomask and the transmitted image of the third area of the same photomask simultaneously.

2. An inspection apparatus according to claim 1, wherein said illumination system comprises a transmission illumination system arranged at the rear surface side of the photomask to direct the transmission illumination beam onto the rear surface of the photomask, and a reflection illumination system arranged at the pattern formed surface side of the photomask to direct the reflection illumination beam onto the pattern formed surface of the photomask.

3. An inspection apparatus according to claim 2, wherein said transmission illumination system comprises a field stop having an opening which is centered on the optical axis, and said reflection illumination system comprises a field stop having an opening which is positioned so as to be displaced from the optical axis.

4. An inspection apparatus according to claim 3, wherein said apparatus comprises an objective lens arranged to be opposed to the pattern formed surface of the photomask, and wherein said transmission illumination beam is directed onto the entire field of view of the objective lens and the reflection illumination beam is directed onto substantially a half of the field of view of the objective lens.

5. An inspection apparatus according to claim 1, wherein there is no spacing between the second area and the third area.

6. A inspection apparatus according to claim 4, wherein the reflection illumination beam is directed onto the pattern formed surface of the photomask through the objective lens.

7. An inspection apparatus according to claim 1, wherein said first image sensor captures the composite image consisting of the reflected image of the light intercepting patterns which are formed on the pattern formed surface and the transmitted image of the transparent patterns of the photomask.

8. An inspection apparatus according to claim 1, wherein said light directing system includes a reflecting element which divides the incident beam into the composite light emitted from the second area and the transmitted light emitted from the third area.

9. An inspection apparatus according to claim 1, wherein said photomask is arranged on the stage which moves in a predetermined direction, and said illumination system is fixed.

10. An inspection apparatus according to claim 9, wherein said first and second image sensors comprise a TDI sensor.

11. An inspection apparatus according to claim 1, wherein said processor subtracts data of the transmitted image outputted from the second image sensor from data of the composite image outputted from the first image sensor in order to form the data of the reflected image of the photomask.

12. An inspection apparatus according to claim 11, wherein said photomask is arranged on a stage which moves along a first direction, and said composite image of the second area and said transmitted image of the third area are captured by a TDI sensor.

13. An inspection method for inspecting a photomask having a pattern formed surface on which light intercepting patterns are formed and a rear surface opposite to the pattern formed surface, so as to detect defects existing on the photomask, the method comprising;

providing a transmission illumination beam and a reflection illumination beam simultaneously;

directing respectively the transmission and reflection illumination beams onto the photomask from opposite sides of the photomask, wherein said transmission illumination beam illuminates a first larger area of the photomask, and the reflection illumination beam illuminates a second smaller area of the photomask which overlaps with a part of the first area, so that composite light including transmitted light through the photomask and reflected light by the photomask emanates from the second area, and the transmitted light through the photomask emanates from a third area which is the remaining area of the first area except the second area;

detecting said composite light emitted from the second area and the transmitted light emitted from the third area so as to capture a composite image consisting of a transmitted image and a reflected image of the second area of the photomask and a transmitted image of the third area of the photomask, respectively; wherein said composite image consisting of the transmitted and reflected images of the second area and the transmitted image of the third area are captured simultaneously.

14. An inspection apparatus according to claim 13, wherein there is no spacing between the second area and the third area.

15. An inspection method according to claim 13, wherein said composite image consists of the reflected image of light intercepting patterns formed on the photomask and the transmitted image of the transparent patterns on which no light intercepting pattern is formed.

* * * * *